US010939690B2

(12) United States Patent
Meisner et al.

(10) Patent No.: US 10,939,690 B2
(45) Date of Patent: Mar. 9, 2021

(54) METHOD FOR PRODUCING A COLLAGENOUS MATERIAL IN PARTICLE FORM

(71) Applicant: GELITA AG, Eberbach (DE)

(72) Inventors: Thomas Meisner, Heidelberg (DE); Arend Willem Sloot, Heidelberg (DE)

(73) Assignee: Gelita AG, Eberbach (DE)

( * ) Notice: Subject to any disclaimer, the term of this patent is extended or adjusted under 35 U.S.C. 154(b) by 109 days.

(21) Appl. No.: 16/185,553

(22) Filed: Nov. 9, 2018

(65) Prior Publication Data

US 2019/0075818 A1   Mar. 14, 2019

Related U.S. Application Data

(63) Continuation of application No. PCT/EP2017/053214, filed on Feb. 14, 2017.

(30) Foreign Application Priority Data

May 18, 2016 (DE) .................... 10 2016 109 094.8

(51) Int. Cl.
A23J 1/10 (2006.01)
A23K 10/26 (2016.01)
A23L 29/281 (2016.01)
A23K 50/42 (2016.01)
C07K 14/78 (2006.01)
C08H 1/06 (2006.01)

(52) U.S. Cl.
CPC ................ *A23J 1/10* (2013.01); *A23K 10/26* (2016.05); *A23K 50/42* (2016.05); *A23L 29/284* (2016.08); *C07K 14/78* (2013.01); *C08H 1/06* (2013.01); *A23V 2002/00* (2013.01); *A23V 2200/00* (2013.01); *A23V 2200/222* (2013.01); *A23V 2200/242* (2013.01); *A23V 2200/244* (2013.01); *A23V 2250/00* (2013.01); *A23V 2250/5422* (2013.01); *A23V 2250/5432* (2013.01)

(58) Field of Classification Search
CPC . A23J 1/10; A23K 50/42; A23K 10/26; A23L 29/284; C07K 14/78; A23V 2002/00; A23V 2200/00; A23V 2200/222; A23V 2200/242; A23V 2200/244; A23V 2250/00; A23V 2250/5422; A23V 2250/5432
See application file for complete search history.

(56) References Cited

U.S. PATENT DOCUMENTS

| 2003/0004315 A1* | 1/2003 | Macdonald ............. A61P 43/00 530/356 |
| 2004/0010122 A1 | 1/2004 | Nnanna et al. |
| 2011/0135699 A1 | 6/2011 | Dick et al. |
| 2012/0114570 A1* | 5/2012 | Bakar ..................... A61P 29/00 424/59 |

FOREIGN PATENT DOCUMENTS

| CN | 101 589 821 A | | 12/2009 |
| CN | 101 787 078 A | | 7/2010 |
| CN | 103554248 | * | 2/2014 |
| DE | 836 982 C | | 4/1952 |
| DE | 60 215 194 T2 | | 8/2007 |
| DE | 10 2008 036 576 A1 | | 2/2010 |
| EP | 1 423 016 B1 | | 10/2006 |

OTHER PUBLICATIONS

Schmidt et al. Collagen Extraction Process. International Food Research Journal. vol. 23. pp. 913-922 (2016).*
Nagai et al. Characterization of Collagen from Emu. Food Science Technology. 2015. vol. 52; pp. 2344-2351.*
Wang et al. Characterization of Collagen from the Skin of Amur Sturgeon. 2014. Food Hydrocolloids. vol. 38. pp. 104-109.*
Kaewdang et al. Characteristics of Collagens from the Swim Bladders of Yellowfin Tuna. 2014. Food Chemistry. vol. 155. pp. 264-270.*
International Bureau, English translation of International Preliminary Report on Patentability in International Application No. PCT/EP2017/053214, dated Nov. 29, 2018.
Gojkovic et al., "Use of ultrasonic spectroscopy and viscosimetry for the characterization of chicken skin collagen in comparison with collagens from other animal tissues," *Prep. Biochem. and Biotech.*, 44(8): 761-771 (2014).
Hashim et al., "Collagen in food and beverage industries," *IFRJ*, 22(1): 1-8 (2016).
International Bureau, International Search Report in International Application No. PCT/EP2017/053214, dated May 8, 2017.

* cited by examiner

Primary Examiner — Anthony J Weier
(74) Attorney, Agent, or Firm — Leydig, Voit & Mayer

(57) ABSTRACT

A method for producing a collagenous material in particle form, includes:
   extracting a collagen- and fat-containing animal raw material using an aqueous extraction solution;
   optionally separating at least one part of the aqueous phase from the extraction residue;
   separating the extraction residue into a collagenous solid phase, an aqueous phase, and a fat phase;
   mixing at least one part of the collagenous solid phase with at least one part of the aqueous phase;
   at least partly drying the mixed phases; and
   comminuting the dried phases in order to obtain the collagenous material in particle form.

9 Claims, No Drawings

METHOD FOR PRODUCING A COLLAGENOUS MATERIAL IN PARTICLE FORM

CROSS-REFERENCE TO RELATED APPLICATIONS

This patent application is a continuation of International Patent Application No. PCT/EP2017/053214, filed Feb. 14, 2017, which claims the benefit of German Patent Application No. 10 2016 109 094.8, filed May 18, 2016, which are each incorporated herein by reference.

FIELD OF THE INVENTION

The present invention relates to a method for producing a collagenous material in particle form.

The invention further relates to a collagenous material in particle form produced according to this method.

BACKGROUND OF THE INVENTION

In the production of various foods, particularly industrial food products, it has long been known that the properties of the food, such as its consistency and texture, can be selectively improved by means of certain protein-based additives. An example of this application are collagen-based materials, which are capable of both binding water and assuming the function of an emulsifier. These additives are referred to as functional proteins because they are used in foods for their food technology properties (and not primarily because of their nutritional value).

Such collagenous materials in particle form, which are used in food products as functional proteins, have until now been directly produced from a collagen-containing animal raw material by reducing said material to the desired particle size by means of a suitable process (e.g. wet or dry grinding). The raw materials primarily used in this connection are the skin and bones of animals. In Unexamined Patent Application DE 102008036576 A1, for example, a method is described for producing collagen particles from a solid collagenous material, more particularly ossein. Such collagen particles can more particularly be used in reduced-fat meat and sausage products in order to contribute as a fat substitute toward the typical texture of fat-containing foods.

BRIEF SUMMARY OF THE INVENTION

An object of the present invention is to propose an effective production method for a collagenous material in particle form.

This object is achieved by the invention by means of a method comprising the following steps:

extracting a collagen- and fat-containing animal raw material using an aqueous extraction solution;

optionally separating at least one part of the aqueous phase from the extraction residue;

separating the extraction residue into a collagenous solid phase, an aqueous phase, and a fat phase;

mixing at least one part of the collagenous solid phase with at least one part of the aqueous phase;

at least partly drying the mixed phases; and comminuting the dried phases in order to obtain the collagenous material in particle form.

DETAILED DESCRIPTION OF THE INVENTION

The first step of the method according to the invention constitutes the essential step in the known production of gelatin. In this step, the soluble portion of the collagen or the portion that can be converted to a soluble form under the extraction conditions is separated from the raw material, and the extraction solution is then concentrated and dried. In other words, the purpose of the invention is to also use the extraction residue in gelatin production (completely or partially) for production of the collagenous material in particle form.

By means of this approach, the invention allows significantly higher added value to be obtained from the animal raw material used, which in this manner is almost completely processed into high-quality products (gelatin and collagen particles) that can be used in the area of food products. In contrast, in production of gelatin according to the prior art, the extraction residue is used only as an additive to fertilizers or animal feed (for livestock and pets).

On the other hand, it was found that despite its different composition, the collagenous material produced according to the present invention has substantially the same advantageous properties as a functional protein as a prior art collagenous material produced by comminution of the non-extracted raw material.

In a preferred embodiment of the invention, the extraction residue is repeatedly extracted with an aqueous extraction solution after separation of the aqueous phase, wherein at least one part of the collagenous solid phase of the last extraction residue is mixed with at least one part of the aqueous phase of the last extraction step. The aqueous phases of the preceding extraction steps can then be included in normal gelatin production. Multiple extraction is a common process in gelatin production, wherein in the individual extraction steps, gelatin of differing quality (more particularly, of different gel strengths) is sometimes obtained.

In the context of the present method, extraction is preferably carried out two to eight times. By means of the number of extraction steps, the properties of the produced collagenous material can be substantially influenced, as the content of soluble or extractable collagen in the final product decreases with an increasing number of extractions.

The aqueous extraction solution is either an acidic solution, which more particularly comprises sulfuric acid or hydrochloric acid, or an alkaline solution, which more particularly comprises calcium hydroxide. Both acidic and alkaline extraction have long been known in the production of gelatin, with the first process producing gelatin of type A and the second gelatin of type B. More particularly, the decision as to which of the two methods to use also depends on the type of raw material used.

The properties of the produced collagenous material can more particularly be influenced within the framework of the present invention by means of the specific extraction conditions, i.e. above all the temperature, pH, and duration of extraction. The possible individual effects of these parameters are presented below by means of exemplary embodiments.

The collagen- and fat-containing animal raw material is preferably selected from the skin and subcutaneous tissue of mammals, birds, and fish. Particularly preferred is the use of pork rinds or cattle split, which are used on a large scale in gelatin production. In the case of these materials, acidic extraction is typically carried out, wherein the aqueous extraction solution preferably has a pH of 3.5 to 5.5, and more preferably 4 to 5.

The extraction time is preferably up to 30 h, more preferably up to 25 h, and in particular 15 to 25 h.

The raw material is preferably comminuted before extraction in the usual manner, for example to a size in the range of approximately 5×5 cm.

After separation of the (last) extraction residue into a fat phase, a collagenous solid phase, and a liquid phase, the latter two phases are mixed with each other according to the method of the invention, wherein optionally, only one part of the resulting phases is used, i.e. the mixing ratio is selectively set. In this connection, the ratio by weight of the collagenous solid phase to the aqueous phase is preferably in the range of 1:99 to 1:1, and more preferably 1:9 to 1:2. The properties of the produced collagenous material can also be influenced by selection of this mixing ratio, and more particularly, the viscosity of the product can be reduced by means of a higher content of the aqueous phase (see the exemplary embodiments below).

Drying of the mixed phases is preferably carried out to a residual water content of 2 to 20 wt %, and more preferably 5 to 15 wt %. A lower water content increases the storage stability of the material and also affects its functionality, more particularly its water absorption capacity.

Drying is preferably carried out at a temperature of 50 to 150° C. The usual methods may be used. More particularly, suitable drying methods are roller drying, spray drying, and disk drying.

Comminuting of the dried phase preferably comprises grinding. The collagenous material is preferably ground to an average particle size of 20 to 250 μm, and more preferably 50 to 150 μm. This size range is particularly suitable in use in food products in order to exert a positive influence on their texture.

The present invention further relates to a collagenous material in particle form produced according to the above-described method. Particular advantages of the collagenous material were described above in connection with the production method.

The average particle size of the collagenous material according to the invention is preferably 20 to 250 μm, and more preferably 50 to 150 μm.

The collagenous material according to the invention preferably has a water absorption capacity of 1:1 to 50:1 based on its net weight.

Moreover, the material preferably has an emulsifying capacity for fat and water of 1:1 to 20:1 respectively based on its net weight.

Finally, the invention also relates to use of the collagenous material according to the invention in particle form in the production of food products, more particularly meat and sausage products. In addition, the collagenous material can also be used in the production of feed products for livestock and pets.

These and other advantages of the invention will be explained by means of the following examples.

EXAMPLES

Example 1

Production of the Collagenous Material

In order to produce the collagenous materials according to the invention described below in particle form, pork rinds were extracted six times with a sulfuric acid extraction solution under the respective conditions indicated. The last extraction residue was divided into a collagenous solid phase, an aqueous phase, and a fat phase, and the solid phase was mixed with the aqueous phase in the respective ratios indicated. After roller drying, the material was comminuted to an average particle size of 150 μm.

Example 2

Effect of pH During Extraction

In the examples according to Table 1, the respective extractions were carried out at a temperature of 65° C. for a duration of 18 h, but at different pH values. The solid and aqueous phases were mixed in a ratio of 3:7.

The results show that pH has a clear effect on the water binding capacity and emulsifying capacity of the collagenous material:

TABLE 1

| pH of extraction | Water binding capacity | Emulsifying capacity |
|---|---|---|
| 3.45 | 130 g | 30 g |
| 3.70 | 550 g | 80 g |
| 4.15 | 1460 g | 165 g |
| 4.50 | 1830 g | 280 g |

The gel strength of a 20 wt % suspension of the collagenous material was taken as a measure of water binding capacity. The suspension was heated to 60° C., and the gel strength after cooling to 10° C. was measured after 20 h.

The gel strength of an emulsion in a ratio of 1:6:6 (collagenous material:fat:water) was taken as a measure for determining emulsifying capacity. The emulsion was prepared at 20° C., and gel strength after cooling to 10° C. was measured after 20 h.

Measurement of gel strength was carried out in each case using a TA.XTplus texture analyzer, Ball SMS P/0.75, at a penetration depth of 1 cm.

Example 3

Effect of Extraction Time

In the examples according to Table 2, the extractions were carried out at a temperature of 65° C. and a pH of 4.8, but with different extraction times. The solid and aqueous phases were mixed in a ratio of 3:7.

The results shows that extraction time also has an effect on the water binding capacity and emulsifying capacity of the collagenous material:

TABLE 2

| Extraction time | Water binding capacity | Emulsifying capacity |
|---|---|---|
| 18 h | 1490 g | 180 g |
| 23 h | 1460 g | 165 g |
| 27 n | 255 g | 40 g |

Determination of water binding capacity and emulsifying capacity was carried out as described above.

Example 4

Effect of Mixing Ratio

In the examples according to Table 3, the respective extractions were carried out at a temperature of 65° C. and a pH of 4.8, and with an extraction time of 18 h. The phases were mixed in different ratios.

The results show that in this manner, the viscosity of an emulsion of the material can be set:

TABLE 3

| Aqueous phase | Collagen-containing solid phase | Viscosity |
|---|---|---|
| 100% | 0% | 0.13 mPa · s |
| 75% | 25% | 1.26 mPa · s |
| 60% | 40% | 4.50 mPa · s |
| 50% | 50% | 10.50 mPa · s |
| 40% | 60% | 42.50 mPa · s |

Determination of viscosity was carried out in a 30 wt % suspension of the collagenous material at 60° C., measured with an Anton Paar MCR 102 rheometer.

The invention claimed is:

1. A method for producing a collagenous material in particle form, comprising:
    extracting a collagen- and fat-containing animal raw material using an acidic aqueous extraction solution having a pH of 3.5 to 5.5, to yield an aqueous phase and an extraction residue;
    separating at least one part of the aqueous phase from the extraction residue;
    repeating the preceding extracting and separating by repeatedly extracting the extraction residue, after separation of the aqueous phase, with an acidic aqueous extraction solution having a pH of 3.5 to 5.5, wherein the extraction is carried out a total of two to eight times;
    separating the extraction residue of a last extraction into a collagenous solid phase, an aqueous phase of the last extraction, and a fat phase;
    mixing at least one part of the collagenous solid phase with at least one part of the aqueous phase of the last extraction in a ratio by weight of 1:99 to 1:1;
    at least partly drying the mixed phases; and
    comminuting the dried phases in order to obtain the collagenous material in particle form with an average particle size of 20 to 250 μm.

2. The method according to claim 1, wherein the duration of extraction is up to 30 h.

3. The method according to claim 1, wherein the collagen- and fat-containing animal raw material is selected from the skin and subcutaneous tissue of any one of mammals, birds, and fish.

4. The method according to claim 1, wherein drying of the mixed phases is carried out to a residual water content of 2 to 20 wt %.

5. The method according to claim 1, wherein drying is carried out at a temperature of 50 to 150° C.

6. The method according to claim 1, wherein comminuting of the dried phases comprises grinding.

7. The method of claim 1, wherein the acidic aqueous extraction solution comprises sulfuric acid or hydrochloric acid.

8. The method of claim 1, wherein the acidic aqueous extraction solution has a pH of 4 to 5.

9. The method of claim 1, wherein the collagenous solid phase and the aqueous phase are mixed with each other in a ratio by weight of 1:9 to 1:2.

* * * * *